United States Patent
Jurczakowski et al.

(10) Patent No.: US 9,221,044 B2
(45) Date of Patent: Dec. 29, 2015

(54) FLOW SYSTEM METHOD FOR PREPARING SUBSTANTIALLY PURE NANOPARTICLES, NANOPARTICLES OBTAINED BY THIS METHOD AND USE THEREOF

(71) Applicant: Uniwersytet Warszawski, Warsaw (PL)

(72) Inventors: Rafal Jurczakowski, Brwinów (PL); Adam Lewera, Warsaw (PL); Pawel Kulboka, Drawsko Pomorskie (PL)

(73) Assignee: UNIWERSYTET WARSZAWSKI, Warsaw (PL)

( * ) Notice: Subject to any disclaimer, the term of this patent is extended or adjusted under 35 U.S.C. 154(b) by 0 days.

(21) Appl. No.: 14/485,023

(22) Filed: Sep. 12, 2014

(65) Prior Publication Data

US 2015/0011655 A1 Jan. 8, 2015

Related U.S. Application Data

(63) Continuation of application No. PCT/IB2013/054857, filed on Jun. 13, 2013.

(51) Int. Cl.
*B22F 9/24* (2006.01)
*B82Y 40/00* (2011.01)
*B01J 35/00* (2006.01)
(Continued)

(52) U.S. Cl.
CPC ............ *B01J 35/0013* (2013.01); *A61K 9/143* (2013.01); *A61K 31/167* (2013.01); *B01J 13/00* (2013.01); *B01J 13/0043* (2013.01); *B01J 13/02* (2013.01); *B01J 23/42* (2013.01); *B01J 23/44* (2013.01); *B01J 23/52* (2013.01); *B01J 23/72* (2013.01); *B01J 23/8926* (2013.01); *B22F 1/0018* (2013.01); *B22F 1/0022* (2013.01); *B22F 1/025* (2013.01); *B22F 9/18* (2013.01); *B22F 9/24* (2013.01); *B82Y 30/00* (2013.01); *C22C 1/0466* (2013.01); *B22F 2203/11* (2013.01); *C22C 1/04* (2013.01); *C22C 1/0425* (2013.01);
(Continued)

(58) Field of Classification Search
None
See application file for complete search history.

(56) References Cited

U.S. PATENT DOCUMENTS 6,783,569 B2 * 8/2004 Cheon et al. .................... 75/348
2006/0054506 A1 3/2006 Natan et al.
(Continued)

FOREIGN PATENT DOCUMENTS

EP 1741717 A1 1/2007
KR 20110019603 A 2/2011
(Continued)

OTHER PUBLICATIONS

Wagner J et al., "Continuous synthesis of gold nanoparticles in a microreactor" Nano Letters, American Chemical Society, pp. 685-691, vol. 5t No. 4 (Apr. 2005).
(Continued)

*Primary Examiner* — George Wyszomierski
(74) *Attorney, Agent, or Firm* — Browdy and Neimark, P.L.L.C.

(57) ABSTRACT

The invention relates to a method of synthesis of substantially pure nanoparticles in a continuous-flow system, in which a precursor substance solution undergoes reduction reaction using a reducing agent solution and nanoparticles are produced, wherein the reduction reaction is terminated by adding an agent neutralizing the reducing agent and a stable nanoparticle colloid is produced. In the method of the invention a need for using surfactants or other organic molecules for nanoparticle stabilization has been eliminated.

23 Claims, 7 Drawing Sheets

(51) Int. Cl.
| | |
|---|---|
| B22F 1/00 | (2006.01) |
| B22F 1/02 | (2006.01) |
| B01J 13/00 | (2006.01) |
| B01J 13/02 | (2006.01) |
| B82Y 30/00 | (2011.01) |
| A61K 9/14 | (2006.01) |
| A61K 31/167 | (2006.01) |
| B01J 23/42 | (2006.01) |
| B01J 23/44 | (2006.01) |
| B01J 23/52 | (2006.01) |
| B01J 23/72 | (2006.01) |
| B01J 23/89 | (2006.01) |
| B22F 9/18 | (2006.01) |
| C22C 1/04 | (2006.01) |
| C22C 5/02 | (2006.01) |
| C22C 5/04 | (2006.01) |
| C22C 9/00 | (2006.01) |
| C22C 29/12 | (2006.01) |

(52) U.S. Cl.
CPC .. *C22C 5/02* (2013.01); *C22C 5/04* (2013.01); *C22C 9/00* (2013.01); *C22C 29/12* (2013.01)

(56) References Cited

U.S. PATENT DOCUMENTS

| | | |
|---|---|---|
| 2007/0207335 A1 | 9/2007 | Karandikar et al. |
| 2008/0081017 A1 | 4/2008 | Zhou et al. |
| 2012/0283336 A1* | 11/2012 | Grigorenko et al. .......... 514/769 |

FOREIGN PATENT DOCUMENTS

| | | |
|---|---|---|
| WO | 2004076056 A2 | 9/2004 |
| WO | 2009133418 A1 | 11/2009 |
| WO | 2010108837 A1 | 9/2010 |

OTHER PUBLICATIONS

Kohler J M et al., "Preparation of metal nanoparticles with varied composition for catalytical applications in microreactors" Chemical Engineering Science, pp. 5048-5055, vol. 63, No. 20 (Oct. 2008).

Kohler J M et al., "Formation of Au/ Ag Nanoparticles in a Two Step Micro Flow-Through Process" Chemical Engineering & Technology, pp. 347-354, vol. 30, No. 3 (Mar. 2007).

Wagner J et al., "Generation of metal nanoparticles in a microchannel reactor", Chemical Engineering Journal, Elsevier, pp. 251-260, vol. 101, No. 1-3 (Aug. 2004).

Ma Xiaoyuan et al., "Biocatalyticcllly induced growth of gold nanoshells: using enzyme reaction for the controllable fabrication of nanomaterials", Journal of Nanoscience and Nanotechnology, American Scientific Publishers, pp. 870-878, vol. 12, No. 2 (Feb. 2012).

Eluri Ravi et al., "Synthesis of nickel nanoparticles by hydrazine reduction: mechanistic study and continuous flow synthesis", J Nanopart Res, pp. 1-14, vol. 14, No. 800, (Mar. 2012).

Carkner Andrew, "Green Metal Nanoparticle Synthesis" Chemical Engineering, McGill University, pp. 1-75, (Apr. 2008).

Liu Zhiguo et al., "Synthesis of micron-scale gold nanochains by a modified citrate reduction method", Applied Surface Science, pp. 5827-5830, vol. 255, (Jan. 2009).

Solarska et al., R., "Silver Nanoparticle Induced Photocurrent Enhancement at WO3 Photoanodes", Angewandte Chem. Int. Ed., vol. 49, No. 43, pp. 7980-7983, (2010).

Park et al., J., "The Role of Organic Capping Layers of Platinum Nanoparticles in Catalytic Activity of CO Oxidation", Catalysis Letters, vol. 129, No. 1-2, pp. 1-6, (2009).

Bjorksten et al., U., "Photoelectrochemical Studies on Nanocrystalline Hematite Films", Chem. Mater, vol. 6, pp. 858-863, (1994).

Solla-Gullon et al., J., "Electrochemical characterisation of platinum nanoparticles prepared by microemulsion: how to clean them without loss of crystalline surface structure", Journal of Electroanalytical Chemistry, vol. 491, pp. 69-77, (2000).

Weng et al., Chen-Hsun, "Synthesis of hexagonal gold nanoparticles using a microfluidic reaction system", J. Micromech. Microeng. vol. 18, pp. 1-8, (2008).

Torigoe et al., Kanjiro, "Microflow reactor synthesis of palladium nanoparticles stabilized with poly(benzyl ether) dendron ligands", Journal of Nanoparticle Research, vol. 12, No. 3, pp. 951-960, (2010).

Kelly et al., K. Lance, "The Optical Properties of Metal Nanoparticles: The Influence of Size, Shape, and Dielectric Environment", J. Phys. Chem. B, vol. 107, No. 3, pp. 668-677, (2003).

Yang et al., Sung-Yi, "Size-controlled synthesis of gold nanoparticles using a micro-mixing system", Microfluid Nanofluid, vol. 8, pp. 303-311, (2010).

Mott et al., Derrick, "Synthesis of Size-Controlled and Shaped Copper Nanoparticles", Langmuir 2007, vol. 23, pp. 5740-5745, (2007).

Paracchino et al., Adriana, "Highly active oxide photocathode for photoelectrochemical water reduction", Nature Materials, vol. 10, pp. 456-461, (2011).

Song et al., Yujun, "Synthesis of Palladium Nanoparticles Using a Continuous Flow Polymeric Micro Reactor", Journal of Nanoscience and Nanotechnology, vol. 4, No. 7, pp. 788-793, (2004).

Wojnicki et al., M., "Gold Nanoparticles Synthesis in a Flow Microreactor Stabilized With PVA (Polyvinyl Alcohol)", Rudy Metale R54, No. 12, pp. 848-852, (2009).

Wojnicki et al., M., "Application of Flow Microreactors for Synthesis of Noble Metals Nanoparticles (Pt, Pd, Au) Review", Rudy Metale, vol. 56, No. 12, pp. 745-752, (2011).

Streszewski et al., B., "Gold Nanoparticles Synthesis in the Flow Microreactor System Via Gold(III) Complex Ions Reduction Using Hydrazine", Rudy Metale, vol. 56, No. 12, pp. 752-761, (2011).

Szabo, S., "Underpotential Deposition of Metals on Foreign Metal Substrates", International Reviews in Physical Chemistry, vol. 10, No. 2, pp. 207-248, (1991).

Polish Office Action in corresponding application No. P399505 (Jul. 2012).

* cited by examiner

FLOW SYSTEM METHOD FOR PREPARING SUBSTANTIALLY PURE NANOPARTICLES, NANOPARTICLES OBTAINED BY THIS METHOD AND USE THEREOF

TECHNICAL FIELD

The invention provides a flow system method for preparing substantially pure nanoparticles, nanoparticles obtained by this method and use thereof.

BACKGROUND ART

In recent years nanomaterials have become a subject of significant interest due to their size-dependent properties and potential application in the field of catalysts, sensors and other fields of nanotechnology and microelectronics. Nanoparticles of metals or their alloys with diameter ranging from several to several dozens of nanometers are of particular interest. Metallic nanoparticles display increased reactivity of the surface atoms and exceptional optical properties. Moreover, because of their highly developed surface area, nanoparticles are considered an attractive material for use in heterogenic catalysis. Metallic nanoparticles can also be used in medicine as carriers for therapeutic substances.

Different methods of nanoparticle synthesis are known. One of such methods utilizes continuous-flow microreactors. A continuous-flow microreactor is a device used for carrying out a chemical reaction in a small volume. It comprises one or more channels of small diameter for transporting the reagents in and the product out of the system, as well as a mixing compartment or a combination of mixing compartments, which allow for the mixing of the reagents. Use of such type of a device has many advantages, as it allows for quick and thorough mixing of the reagents and makes the temperature control easy. The continuous-flow microsystems for nanoparticle synthesis have been described, for example in publication WO 2004/076056 and WO 2009/133418. Use of continuous-flow microsystems for synthesis of nanoparticles of noble metals, such as Pt, Pd and Au, has been discussed in a review article by Wojnicki M. et al. ("Zastosowanie mikroreaktorów przepływowych do syntezy nanocząstek metali szlachetnych (Pt, Pd, Au). Przegląd literatury", Rudy Metale, 2011, vol. 56, no 12, p. 745-752).

Methods for nanoparticle synthesis using continuous-flow microreactors comprise chemical reduction of metal precursors, i.e. metal salts, such as $Pd(OAc)_2$, $PdCl_2$, $PtCl_4$, $AuCl_3$, $AgNO_3$, $Cu(OAc)_2$, $CuCl_2$, $RhCl_3$ and $FeCl_3$, in a solution and in the presence of surfactants or other organic molecules, which aim to stabilize nanoparticles (their concentration and type determine nanoparticle size) and prevent nanoparticle aggregation.

Sodium citrate, ascorbic acid, hydrazine, sodium borohydride, lithium tetraethylborohydride, methyl alcohol, ethylene glycol, 1,2-hexadecandiol and glucose are commonly used as reducing agents (see, for example Streszewski B. et al., "Synteza nanocząstek złota metodą redukcji jonów kompleksowych złota (III) za pomocą hydrazyny w układzie mikroreaktora przepływowego", Rudy Metale, 2011, vol. 56, no 12, p. 752-761).

Polyvinylpyrrolidone (PVP) (as discussed in, for example, in Wagner J. et al., "Generation of metal nanoparticles in a microchannel reactor", Chemical Engineering Journal, 2004, no 101, p. 251-260; Köhler J. M. et al., "Formation of isolated and clustered Au nanoparticles in the presence of polyelectrolyte molecules using a flow-through Si chip reactor", Journal of Materials Chemistry, 2005, no 15, p. 1924-1930; Wagner J. et al., "Continuous synthesis of gold nanoparticles in a microreactor", Nano Letters, 2005, vol. 5, no 4, p. 685-691.) and polyvinyl alcohol (PVA) (as discussed in, for example, in Köhler J. M. et al., "Formation of Au/Ag Nanoparticles in a Two Step Micro Flow-Through Process", Chem. Eng. Technol. 2007, vol. 30, no 3, p. 347-354; Köhler J. M. et al., "Preparation of metal nanoparticles with varied composition for catalytically applications in microreactors", Chemical Engineering Science, 2008, vol. 63, p. 5048-5055; Wojnicki M. et al., "Synteza nanocząstek złota stabilizowanych PVA (alkohol poliwinylowy) w mikroreaktorze przepływowym"; Rudy Metale, 2009, vol. 54, no 12, p. 848-852) are often used as stabilizing agents. Other stabilizing agents used in the art include sulfobetaine (Song Y. et al., "Synthesis of palladium nanoparticles using a continuous flow polymeric microreactor", Journal of Nanoscience and Nanotechnology, 2004, vol.4, no 7, p. 788-793) and poly(benzyl ether) (Torgoe K. et al., "Microflow reactor synthesis of palladium nanoparticles stabilized with poly(benzyl ether) Dendron ligands", Journal of Nanoparticle Research, 2010, vol. 12, no 3, p. 951-960). Sometimes a reducing agent can, at the same time, play a role of a stabilizing agent, as it is in the case of sodium citrate (Weng C. H. et al., "Synthesis of hexagolan gold nanoparticles using a microfluidic reaction system", Journal of Micromechanics and Microengineering, 2008, vol. 18, p. 1-8; Sung-Yi Yang, "Size controlled synthesis of gold nanoparticles using a micromixing system", Microfluid Nanofluid, 2009, vol. 8, p. 303-311).

Straightforward size control of the produced nanoparticles is an advantage of using continuous-flow microsystems for nanoparticle synthesis. Nanoparticle size depends on temperature, reagent flow rate and length of the channels, where reduction reaction takes place. Use of surfactants and other organic molecules as stabilizing agents is a disadvantage of nanoparticle synthesis methods known in the art. Use of stabilizing agents is very unfavorable, because they strongly adsorb on the surface of the newly formed nanoparticles and before further use of the nanoparticles it is necessary to use complex procedures, for example electrochemical methods, to purify their surface (see, for example, publication of Solla-Gullon J. et al., "Electrochemical characterization of platinum nanoparticles prepared by microemulsion: how to clean them without loss of crystalline surface structure", J. Electroanal. Chem., 2000, vol. 491, no 1-2, p. 69-77), and this, very often, alters the nanoparticle properties (for example, catalytic properties). Furthermore, very often it is not possible to remove the adsorbed stabilizing agents entirely from the nanoparticle surface (see, for example, Park, J. Y. et al., "The Role of Organic Capping Layers of Platinum Nanoparticles in Catalytic Activity of CO Oxidation", Catalysis Letters 2009, vol. 129, no 1-2, p. 1-6).

A further disadvantage related to use of continuous-flow microsystems known in the art is that they are limited to low reagent concentrations, which results in obtaining of colloids having low concentration of nanoparticles.

Therefore there exists a considerable demand for a method enabling nanoparticle synthesis, in particular nanoparticles of metals or their alloys, in essentially pure form, which method would make it possible to use such nanoparticles directly, i.e. without the need of performing the inconvenient purification processes. It would be also advantageous, if a method was developed, whose application would lead to obtaining stable nanoparticle colloids of high concentration and would make it possible to produce nanoparticles on a large scale.

DISCLOSURE OF INVENTION

The inventors of the present invention have developed a synthesis method for producing substantially pure nanoparticles, which method makes it possible to control size of the synthesized nanoparticles and at the same time eliminates the need to use the stabilizing agents, in particular stabilizing agents in the form of surfactants and other organic molecules. Moreover, this method results in nanoparticles in the form of colloids having high concentration of nanoparticles, the said colloids being characterized by high stability. This method further makes it possible to produce the nanoparticles on a large scale.

The invention relates to a method of synthesis of substantially pure nanoparticles of controlled size in a continuous-flow system, wherein the said continuous-flow system comprises tubing, in which the stream or reagents and products flows in a continuous manner, and wherein the said method comprises at least one step, in which a precursor substance solution undergoes reduction reaction using a reducing agent solution and nanoparticles are produced, and wherein the reduction reaction is terminated after the last step by adding an agent neutralizing the reducing agent (also called a terminator) and a nanoparticle colloid is produced. Examples of continuous-flow systems used to carry out the method of the invention are presented schematically in FIG. 1a and FIG. 1b.

Figure 1A:
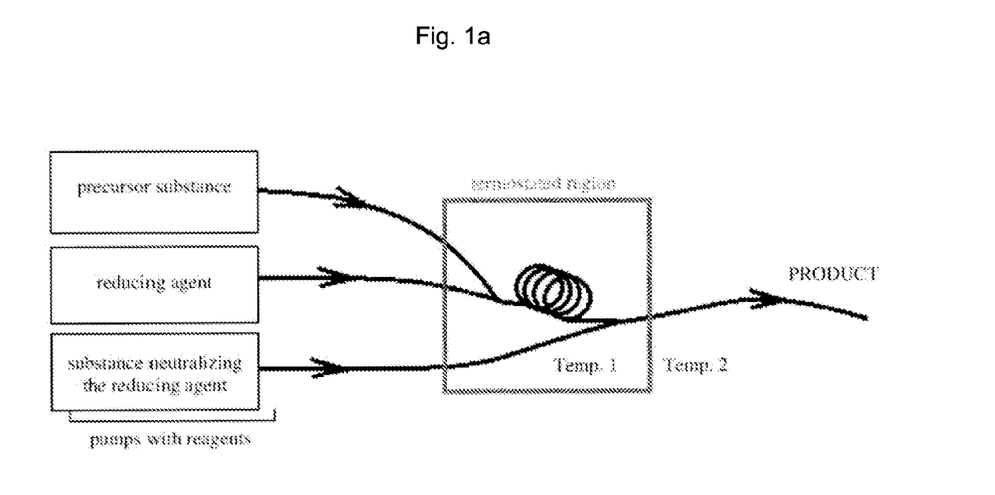
FIG. 1a presents a scheme of the continuous flow system for synthesis of the substantially pure homogenous nanoparticles that is used in the method of the invention.

In the preferred embodiment the method of the invention comprises one step, in which the precursor substance solution undergoes reduction reaction using the reducing agent solution and homogeneous nanoparticles are obtained. The term "homogeneous nanoparticles" should be understood as nanoparticles having uniform atom distribution throughout the entire volume of the nanoparticle. The homogeneous nanoparticles include, in particular, both the metal nanoparticles, as well as metal alloy nanoparticles. FIG. 1a presents a system, in which the method comprising one reduction step is carried out. In this system the tube, in which the reducing agent solution is flowing, is fed with the precursor substance solution through a different tube. After mixing of the two solutions, nanoparticles are formed as a result of the reduction reaction. These formed nanoparticles flow together with the stream of the reaction mixture in the direction of the site, where the tube feeding the substance neutralizing the reducing agent is connected. The nanoparticle colloidal solution flows out of the system.

Figure 1B:
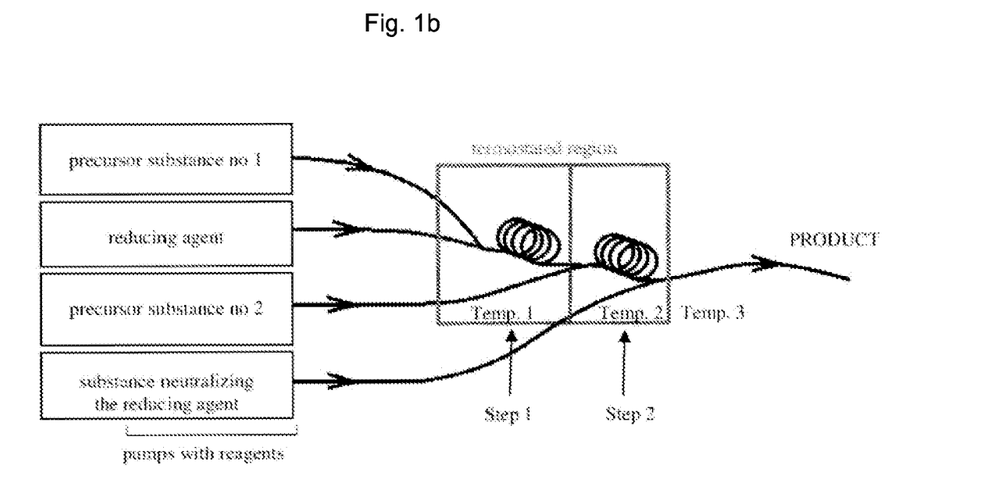
FIG. 1b presents a scheme of the continuous flow system for synthesis of the substantially pure core-shell nanoparticles that is used in the method of the invention.

In another preferred embodiment the method of the invention comprises at least two steps, in which the precursor substance solution undergoes reduction reaction using the reducing agent solution and layered nanoparticles of core-shell type are obtained. FIG. 1b presents a system, in which the method comprising two reduction steps is carried out. In this system the tube, in which the reducing agent solution is flowing, is fed with the solution of the first precursor substance (precursor substance 1) through a different tube. After mixing of the two solutions nanoparticles, which constitute the core, are formed as a result of the reduction reaction (step no 1). These formed nanoparticles flow together with the stream of the reaction mixture in the direction of the site, where the tube feeding the second precursor substance (precursor substance 2) is connected. The reduction of the second precursor substance (step no 2) results in formation of the shell made of a different substance on the nanoparticles formed in the first step. The layered nanoparticles flow with the stream of the reaction mixture in the direction of the site, where the tube feeding the substance neutralizing the reducing agent is connected. The colloidal solution of the core-shell nanoparticles flows out of the system.

Also, as the substance neutralizing the reducing agent, a redox buffer can possibly be used having a potential at which the reducing agent becomes oxidized. A possibility to control precisely the potential of the colloid solution is an advantage resulting from using the redox buffer. The redox potential control of the colloid solution makes the control of the nanoparticle surface charge possible, and thus it is possible to select appropriate conditions under which the colloid is stable. Also formation of the outer shell consisting of an atomic monolayer deposited on the core of a different metal is also possible when the redox buffer is used. In order to do that it is necessary to prepare a colloid of nanoparticles, which nanoparticles constitute the cores, wherein to the said colloid a redox buffer is added having a potential suitable for under-potential reduction (i.e. Under-Potential Deposition, UPD) of the metal outer layer (i.e. shell) on the metal of the core. At the same time, the buffer potential has to be high enough to prevent the over-potential reduction (i.e. Over-Potential Deposition, OPD) of the metal outer layer, and thus the formation of the subsequent metal layers of the shell is avoided. In case of the most of the noble metals the UPD and OPD processes are noticeably separated on the potential scale and this method is used for monolayer deposition on the surface of metallic electrodes, whose potential is controlled by the means of a potentiostat (see, for example, S. Szabó, "Under-potential deposition of metals on foreign metal substrates", International Reviews in Physical Chemistry 1991, vol. 10, no 2, p. 207-248).

As used herein the phrase "substantially pure nanoparticles" refers to the nanoparticles on surface of which neither surfactants nor other organic molecules are adsorbed. Not limiting to any theory, it can be stated that nanoparticles obtained by the method of the invention are stabilized by addition of the substance neutralizing the reducing agent to the reaction system, due to a rapid elimination of the reducing agent and as a result of formation of hydrated oxides and/or hydroxides and/or hydroxysalts on the surface of the nanoparticles. Use of the precursor substances that do not provide the reaction mixture with ions, which could strongly adsorb on the surface of the nanoparticles formed in the reduction process, is particularly preferred.

The method of the invention can be used, in particular, in the synthesis of nanoparticles of metals and their alloys. Therefore, in the preferred embodiment, the precursor substance is a metal precursor or a mixture of metal precursors, preferably a metal salt or a mixture of different metal salts. The method of the invention is preferably used for the synthesis of metal nanoparticles selected from a group comprising palladium, silver, gold, platinum, ruthenium, osmium, iridium, rhodium, copper, nickel, cobalt and iron, as well as alloys thereof. More preferably, the method of the invention is used for synthesis of nanoparticles of noble metals, i.e. platinum, palladium, ruthenium, osmium, iridium, rhodium, silver and gold, and their alloys. In another, particularly preferred, embodiment copper nanoparticles are obtained.

Semiconductor nanoparticles, such as nanoparticles of copper (I) oxide ($Cu_2O$) and palladium (II) oxide (PdO), are also obtained by the method of the invention. In a particularly preferred embodiment $Cu_2O$ nanoparticles are obtained.

A possibility to synthesize copper (I) oxide is very beneficial, because this material is a p-type semiconductor with a narrow band gap of ~2 eV and attractive Fermi level position for the process of water photolysis. It is widely used as a photocathode material in the photoelectrolytic cells in heterojunction with zinc oxide, as well as in the technology lithium ion batteries. It should be emphasized that $Cu_2O$ has to be coated with a thin layer of another semiconductor, which is resistant to reduction or photoreduction in aqueous solutions at the hydrogen evolution potential. It has recently been shown that $Cu_2O$ can effectively be protected by a thin layer of $TiO_2$ deposited by a method of atomic layer deposition (ALD) (A. Paracchino et al., Nature Materials, 10, 2011, 456-461).

Any substances whose reduction under specific reaction conditions results in nanoparticle formation can be used as a precursor substance in the method of the invention. The preferred precursor substances, whose solutions are used in the method of the invention, are salts selected from a group comprising $AgNO_3$, $AgClO_4$, $AgHSO_4$, $Ag_2SO_4$, $AgF$, $AgBF_4$, $AgPF_6$, $CH_3COOAg$, $AgCF_3SO_3$, $CuCl_2$, $Cu(NO_3)_2$, $CuSO_4$, $Cu(HSO_4)_2$, $Cu(ClO_4)_2$, $CuF_2$, $(CHCOO)_2Cu$, $H_2PtCl_6$, $H_6Cl_2N_2Pt$, $PtCl_2$, $PtBr_2$, $K_2[PtCl_4]$, $Na_2[PtCl_4]$, $Li_2[PtCl_4]$, $H_2Pt(OH)_6Pt(NO_3)_2$, $[Pt(NH_3)_4]Cl_2$, $[Pt(NH_3)_4]$ $(HCO_3)_2$, $[Pt(NH_3)_4](OAc)_2$, $(NH_4)_2PtBr_6$, $K_2PtCl_6$, $PtSO_4$, $Pt(HSO_4)_2$, $Pt(ClO_4)_2$, $H_2PdCl_6$, $H_6Cl_2N_2Pd$, $PdCl_2$, $PdBr_2$, $K_2[PdCl_4]$, $Na_2[PdCl_4]$, $Li_2[PdCl_4]$, $H_2Pd(OH)_6$, $Pd(NO_3)_2$, $[Pd(NH_3)_4]Cl_2$, $[Pd(NH_3)_4](HCO_3)_2$, $[Pd(NH_3)_4](OAc)_2$, $(NH_4)_2PdBr_6$, $(NH_3)_2PdCl_6$, $PdSO_4$, $Pd(HSO_4)_2$, $Pd(ClO_4)_2$, $HAuCl_4$, $AuCl_3$, $AuCl$, $AuF_3$, $(CH_3)_2SAuCl$, $AuF$, $AuCl$ $(SC_4H_8)$, $AuBr$, $AuBr_3$, $Na_3Au(S_2O_3)_2$, $HAuBr_4$, $K[Au(CN)_2]$, $CoF_2$, $Co(NO_3)_2$, $CoCl_2$, $CoSO_4$, $Co(HSO_4)_2$, $Co(ClO_4)_2$, $(CHCOO)_2Co$, $CoBr_2$, $[Co(NH_3)_6]Cl_3$, $[CoCl(NH_3)_5]Cl_2$, $[Co(NO_2)(NH_3)_5]Cl_2$, $NiF_2$, $Ni(NO_3)_2$, $NiCl_2$, $NiSO_4$, $Ni(HSO_4)_2$, $Ni(ClO_4)_2$, $(CHCOO)_2Ni$, $NiBr_2$, $Ni(OH)SO_4$, $Ni(OH)Cl$, $FeF_2$, $Fe(NO_3)_2$, $FeCl_2$, $FeSO_4$, $Fe(HSO_4)_2$, $Fe(ClO_4)_2$, $(CHCOO)_2Fe$, $FeBr_2$, $FeF_3$, $Fe(NO_3)_3$, $FeCl_3$, $Fe_2(SO_4)_3$, $Fe(HSO_4)_3$, $Fe(ClO_4)_3$, $(CHCOO)_3Fe$, $FeBr_3$, $RuCl_2$ $((CH3)_2SO)_4$, $RuCl_3$, $[Ru(NH_3)_5 (N_2)]Cl_2$, $Ru(NO_3)_3$, $RuBr_3$, $RuF_3$, $Ru(ClO_4)_3$, $OsI$, $OsI_2$, $OsBr_3$, $OsCl_4$, $OsF_5$, $OsF_6$, $OsOF_5$, $OsF_7$, $IrF_6$, $IrCl_3$, $IrF_4$, $IrF_5$, $Ir(ClO_4)_3$, $K_3[IrCl_6]$, $K_2[IrCl_6]$, $Na_3[IrCl_6]$, $Na_2[IrCl_6]$, $Li_3[IrCl_6]$, $Li_2[IrCl_6]$, $[Ir(NH_3)_4Cl_2]Cl$, $RhF_3$, $RhF_4$, $RhCl_3$, $[Rh(NH_3)_5Cl]Cl_2$, $RhCl[P(C_6H_5)_3]_3$, $K[Rh(CO)_2Cl_2]$, $Na[Rh(CO)_2Cl_2]$ $Li[Rh(CO)_2Cl_2]$, $Rh_2(SO_4)_3$, $Rh(HSO_4)_3$ and $Rh(ClO_4)_3$, their hydrates or mixtures of these salts and/or hydrates. In the preferred embodiment, the precursor substance is selected from a group consisting of $Pd(NO_3)_2$, $Cu(NO_3)_2$, $HAuCl_4$, $Pt(NO_3)_2$ and $K_2PtCl_4$. In a further preferred embodiment the precursor substance is a mixture of $Pd(NO_3)_2$ and $Pt(NO_3)_2$.

According to the invention a concentration of the precursor substance solution used in the method of the invention is preferably in the range from 1 mM to 1 M, and more preferably amounts to 5 or 10 mM.

Alternatively the precursor substances can be selected in a way resulting in synthesis of semiconductor nanoparticles, for example metal oxide nanoparticles.

In the method of the invention any substance can be used as a reducing agent, provided that under specific reaction conditions it is capable of reducing the precursor substance while being oxidized. The reducing agent used in the method of the invention is preferably selected from a group comprising hydrazine, hydrazine sulfate, hydrazine nitrate, ascorbic acid, sodium borohydride, sodium hypophosphite, lithium tetraethylborohydride, methanol, 1.2-hexadecanediol, hydroxylamine and dimethylborazane DMAB. Hydrazine is the particularly preferred reducing agent used in the method of the invention.

According to the invention a concentration of the reducing agent solution used in the method of the invention is preferably in the range from 0.5 mM to 4 M, and most preferably amounts to 20 mM.

The selection of the substance neutralizing the reducing agent is of particular importance. The substance neutralizing the reducing agent, also called the terminator, is designed to remove rapidly the reducing agent from the reaction system. Therefore, it preferably exhibits oxidizing properties. Not limiting to any theory, the Inventors have found that use of an oxidizing agent as the substance neutralizing the reducing agent is also preferred because it can lead to control of the redox potential of the colloid solution, thus stabilizing the colloid dispersion: under higher potential the Coulomb repulsion of the positively charged nanoparticles exceeds the van der Waals forces of nanoparticle attraction. The selection of the redox potential determines the level of surface charge (the surface charge density of the metal/semiconductor). By alteration of the electrokinetic potential, it is possible to select conditions under which the colloid exhibits extremely high stability. At higher potentials oxidation of the surface of the newly formed nanoparticles takes place (i.e. oxides are formed on the nanoparticle surface), providing stability to the nanoparticles. Hydrolysis products of unreduced metal, hydroxides and hydrated oxides or hydroxysalts may also favor stabilization of the nanoparticles. The hydrated oxides, hydroxides and hydroxysalts do not adsorb strongly on the nanoparticle surface, therefore the said surface can be easily modified further. Oxide formation and/or surface adsorption of hydrated oxides may also prevent nanoparticle aggregation. The process of nanoparticle aggregation is unfavorable and makes further applications of the nanoparticles impossible.

A substance neutralizing the reducing agent used in the method of the invention is preferably selected from a group comprising hydrogen peroxide, oxygen, ozone and $NO_2$. More preferably, the substance neutralizing the reducing agent is supplied to the system in the form of a solution, and most preferably it is the hydrogen peroxide solution.

The choice of the neutralizing substance will also be influenced by properties of the metal of the nanoparticles. For example, the surface of platinum and gold nanoparticles cannot be oxidized using hydrogen peroxide. For this purpose a stronger oxidizing agent should be used, for example ozone.

A redox buffer can also be used as a substance neutralizing the reducing agent, wherein the said redox buffer comprises a redox pair whose oxidized (ox) and reduced (red) form concentration are comparable (i.e. log([ox]/[red])=±2). Example of such redox pairs can include: $Fe(CN)_6^{3-}/Fe(CN)_6^{4-}$, $Fe^{3+}/Fe^{2+}$, $[Co(bipy)_3]^{2+}/[Co(bipy)_3]^{3+}$, $Co(phen)_3^{3+}/Co(phen)_3^{2+}$, $[Ru(bipy)_3]^{3+}/[Ru(bipy)_3]^{2+}$, $[Ru(NH_3)_6]^{3+}/[Ru(NH_3)_6]^{2+}$ $[Ru(CN)_6]^{3-}/[Ru(CN)_6]^{4-}$, $Fe(phen)_3^{3+}/Fe(phen)_3^{2+}$ and $Ce^{4+}/Ce^{3+}$.

The use of a redox buffer comprising nicotinamide adenine dinucleotide (NADH—reduced form, NAD+- oxidized form) is preferred for biomedical applications.

According to the invention a concentration of the solution of a substance neutralizing the reducing agent used in the method of the invention is preferably in the range from 0.1 mM do 10 M, and more preferably amounts to 35 mM or 40 mM or 9.8 M.

In the preferred embodiment the pH of the solution of a substance neutralizing the reducing agent is adjusted by addition of a buffer, acid or base. Selection of an appropriate pH is of particular importance for synthesis of base metal nanoparticles. In other preferred embodiment the pH of the reaction mixture and the final colloid solution can be adjusted by adding a solution of an acid or base to one, two or all solutions of the precursor substance, reducing agent and terminator used in the method of the invention.

It is also possible to supply the reducing agent to the reaction mixture in the gaseous form.

In the method of the invention, it is important to select the precursor substance, reducing agent and substance neutralizing the reducing agent so that they do not become a source of contamination for the newly formed nanoparticles, in particular the source of surfactants or other organic molecules, which during the reaction or afterwards could adsorb on the nanoparticle surface. It is, however, possible to use in the method of the invention salts of lower organic acids, such as acetates, as precursor substances.

Use of the system hydrazine (as a reducing agent) and hydrogen peroxide (as a substance neutralizing the reducing agent) is particularly preferred in the method of the invention, since as a result of hydrazine oxidation by hydrogen peroxide primarily only nitrogen and water are formed.

In the method of the invention the reduction reaction is carried out preferably in temperature in the range from 0 to 100° C., and most preferably in 40° C. The temperature is a significant factor, which influences the size of the synthesized nanoparticles. The inventors have shown that the increase in temperature results in the size increase of the nanoparticles synthesized by the method of the invention and at the same time widens the size distribution of the obtained nanoparticles.

In the preferred embodiment the particular tubing segments of the continuous flow system, through which the stream of the reagents, the reaction mixture and products flow in the flow system are either thermostated or maintained at the room temperature. More preferably, the particular tubing segments of the continuous flow system, through which the stream of the reagents, the reaction mixture and products flow are maintained at different temperatures. In the particularly preferred embodiment of the method of the invention, the stream of products is cooled down, most preferably to room temperature, after the substance neutralizing the reducing agent is supplied to the system.

FIG. 1a presents a continuous flow system, in which the reduction reaction is carried out in the thermostated region having specific temperature (Temp. 1), for example 40° C., whereas the stream of products is adjusted to room temperature (Temp. 2). Of course the reduction reaction in the method of the invention can be carried out in the room temperature. It is also possible to control the temperature of the product stream, in the form of the colloid solution of the homogenous nanoparticles, in a thermostat.

FIG. 1b presents a continuous flow system, in which in the first step the reduction reaction is carried out in the thermostated region having specific temperature (Temp. 1), for example 40° C., in the second step the reduction reaction is carried out in the thermostated region having specific temperature (Temp. 2), for example 50° C., whereas the product stream in the form of the layered core-shell type nanoparticles is adjusted to room temperature (Temp. 3). Temperature Temp. 1 and Temp. 2 can be the same or different. It is also possible to control the temperature of the product stream in a thermostat.

In a particularly preferred embodiment the method is carried out in the aqueous environment, in which metal nanoparticles are formed as a result of reduction of metal aqua complexes.

The method of the invention is preferably carried out in a continuous flow system, in which the inner diameter of the tubes ranges from 2" to 1/64", preferably from 1/8" to 1/32". As tubing having greater diameter is employed, it is possible not only to use higher reagent concentration, but also to obtain colloid solution of nanoparticles of high concentration. Thus it is possible to use the method of the invention on a large scale. The method of the invention can also be used in the microflow systems, in which the diameter of the channels is several or several dozens micrometers in diameter.

The method of the invention is preferably carried out in the continuous flow system, in which the length of tubes, wherein the reduction reaction takes place, ranges from 1 cm to 5 m, more preferably from 40 cm to 60 cm.

In the preferred embodiment the reagent flow rate in the continuous flow system, wherein the method of the invention is carried out, ranges from 1 ml/h to 100 l/h, more preferably from 200 ml/h to 3200 ml/h.

The length of the tubes, in which the reduction reaction takes place, and the reagent flow rate in the continuous flow system are selected in such a manner, so that an appropriate reduction reaction time is ensured. Preferably the reduction reaction time ranges from 0.01 s to 1 h.

Most preferably, palladium nanoparticles are obtained by the method of the invention, wherein in the method 10 mM $Pd(NO_3)_2$ is used as a precursor substance, 20 mM hydrazine is used as a reducing agent and 35 mM hydrogen peroxide is used a substance neutralizing the reducing agent.

Alternatively copper (I) oxide nanoparticles are obtained by the method of the invention, wherein in the method 10 mM $Cu(NO_3)_2$ is used as a precursor substance, 20 mM hydrazine is used as a reducing agent and 3.79 mM hydrogen peroxide is used a substance neutralizing the reducing agent supplemented with 2.69 mM NaOH (pH≈12). The pH of the obtained nanoparticle colloid solution was about 7.

Moreover, gold nanoparticles are obtained by the method of the invention, wherein in the method 5 mM $HAuCl_4$ is used as a precursor substance, 3 mM hydrazine is used as a reducing agent and 9.8 M hydrogen peroxide is used as a substance neutralizing the reducing agent.

Platinum nanoparticles are also obtained by the method of the invention, wherein in the method 10 mM $K_2PtCl_4$ is used as a precursor substance, 20 mM hydrazine is used as a reducing agent and 40 mM hydrogen peroxide is used a substance neutralizing the reducing agent.

In a further embodiment homogeneous Pd/Pt alloy nanoparticles are obtained by the method of the invention as a result of the reduction reaction of the mixture of $Pd(NO_3)_2$ and $Pt(NO_3)_2$, which is used as a precursor substance.

In another embodiment in the first step of the method of the invention the solution of $Cu(NO_3)_2$ as a precursor substance undergoes the reduction reaction using hydrazine solution, which results in formation of the copper core, and in the second step to the reaction mixture $Pd(NO_3)_2$ solution as a precursor substance is supplied, whose reduction results in formation of the palladium shells on the copper nanoparticles formed in step 1, and the reduction reaction is terminated by addition of hydrogen peroxide solution and a base, wherein the base concentration is sufficient to ensure neutral pH of the product stream.

In the method of the invention a stable nanoparticle colloid is obtained (stable even for a period longer than 4 months), preferably metal or metal alloy nanoparticle colloid, which is characterized by very high purity and high concentration of the reduced metal (even about 1000 ppm and higher). The concentration of the nanoparticles in the colloid can be controlled through the concentration of the reagents used, especially concentration of the precursor substance. For example, in case of 10 mM concentration of $Pd(NO_3)_2$ the colloid solution was obtained, in which palladium content in the form of nanoparticles amounted to approximately 360 ppm.

The synthesized nanoparticles have diameters in the range from 1 to 50 nm, preferably 1.5 to 30 nm, more preferably 2 to 15 nm, and most preferably form 3 to 10 nm Moreover, the method of the invention makes it possible to obtain nanostructures with specific sizes, because size distribution of the nanoparticles synthesized under specific reaction conditions is relatively narrow. The nanoparticles can be also fractionated from the colloid by centrifugation.

Thus the invention also relates to a stable colloid of substantially pure nanoparticles obtained by the method of the invention.

In the preferred embodiment the method of the invention comprises further a colloid nanoparticle centrifugation and/or drying step, wherein nanoparticle powder is obtained.

Therefore, the invention also relates to the nanoparticles per se obtained in the above described method according to the invention.

As a result of a specific reagent selection the product obtained by the method of the invention is a stable colloid of substantially pure nanoparticles or nanoparticles per se. The fact that the nanoparticles according to the invention are not contaminated by surfactants or other organic molecules enables their direct use (nanoparticles as such or in the form of the obtained colloids). Nanoparticles of the invention, especially metal nanoparticles, are used inter alia as very effective heterogeneous catalysts. Modification of their surface with selected substances, such as therapeutic substances, is also possible. Stable metal nanoparticle colloids can also be used as inks for printing elements to be applied in electronics or as material for SERS studies (especially, for example, Au, Ag, Cu) and in fuel cells as selective catalysts of oxygen reduction (especially nanoparticles of Pt, Pd and Pt/Pd alloys).

Significant purity of the nanostructured materials according to the invention enables their use in photoelectrochemical cells. This applies in particular to metal oxide semiconductor (MOS) nanoparticles. For example, iron (III) oxide is an attractive photoanode material (U. Björkstén et al., Chem. Mater., 1994, 6, 858-863), and copper (I) oxide is a very active photocathode material in cells of this type.

The method of the invention leads to synthesis of copper (I) oxide nanoparticles, which do not comprise surfactants and can be coated with a protective layer obtained, for example, in the process of atomic layer deposition (ALD), as discussed above. It is noteworthy, that until now in the state of the art no method of synthesis of pure $Cu_2O$ have not been disclosed, whereas the surfactants exclude a possibility of using ALD for further nanoparticle surface modification.

Pure Pt and Pd nanoparticles can also find application in photoelectrochemical cells as catalysts of the reaction of hydrogen evolution/storage. Use of nanostructured metals of platinum group significantly improves the photocathode effectiveness. Nanoparticles of Cu and Au, which exhibit the surface plasmon resonance effect, can, in turn, be employed to increase the effectiveness of the photoelectrodes (R. Solarska et al., Angewandte Chem.—Int. Ed., 2010, 49 (43), 7980-7983) or as sensors operating based on a characteristic resonance frequency resulting from alteration of the dielectric environment of the nanoparticles (K. L. Kelly et al., J. Phys. Chem. B, 2003, 107 (3), 668-677). It should be underlined that for such application use of pure nanoparticles is required.

The invention relates, therefore, to use on nanoparticles obtained by the method of the invention in medicine and as heterogeneous catalysts or their use in fuel cells and photoelectrochemical cells.

The above and other advantages and benefits will become more apparent based on the examples of the invention embodiments presented below.

BRIEF DESCRIPTION OF DRAWINGS

The subject of the invention was illustrated in a drawing, in which.

EXAMPLES

Continuous Flow System Used in Examples

Continuous flow system for synthesis of substantially pure nanoparticles used in the method of the invention is presented schematically on FIG. 1a i 1b. It is composed of a set of Teflon tubes, through which the reagents are pumped and the product in the form of the nanoparticle colloid is discharged. Pumps are an important element of this system because they ensure a fixed flow rate of the reagents throughout the system. The region, where reduction of a precursor substance takes place is termostated.

A List of the Used Reagents
- palladium: $Pd(NO_3)_2 \cdot xH_2O$, 99.9%, Alfa Aesar
- hydrazine: $N_2H_4 \cdot H_2O$, 50-60% concentration, Aldrich
- Perhydrol: hydrogen peroxide 30% solution, pure for analysis, Chempur
- copper: $Cu(NO_3)_2 \cdot 3H_2O$ pure for analysis, POCH
- gold: $HAuCl_4$, 99.99%, Alfa Aesar
- platinum: $K_2PtCl_4$, 99.99%, Alfa Aesar
- sodium hydroxide: NaOH, pure for analysis, POCH
- nitric acid: $HNO_3$ 65% pure for analysis, POCH
- sulfuric acid, 99,999%, Sigma Aldrich

Example 1

Synthesis of Palladium Nanoparticles of Controlled Size and Their Properties Characteristic A) Reduction reaction is carried out in the continuous flow system presented in FIG. 1a, in a Teflon tube having the inner diameter of 1/32" and length of 40 cm, wherein the flow rate of the reagents in the reaction tube is 200 ml/h.

Aqueous solution of 10 mM palladium (II) nitrate (Pd $(NO_3)_2$) is used to obtain a stable colloid of palladium nanoparticles. 20 mM aqueous solution of hydrazine is used as the reducing agent.

The reaction is carried out in temperature of 40° C., and 35 mM solution of hydrogen peroxide is used to terminate the reaction.

A stable black colloid of palladium nanoparticles is the product of the reaction. The metal concentration in the obtained colloid amounts to about 360 ppm. The colloid obtained is stable for a period of 4 months (or even longer) without a need for mixing and/or sonication in the ultrasonic bath.

Figure 2:
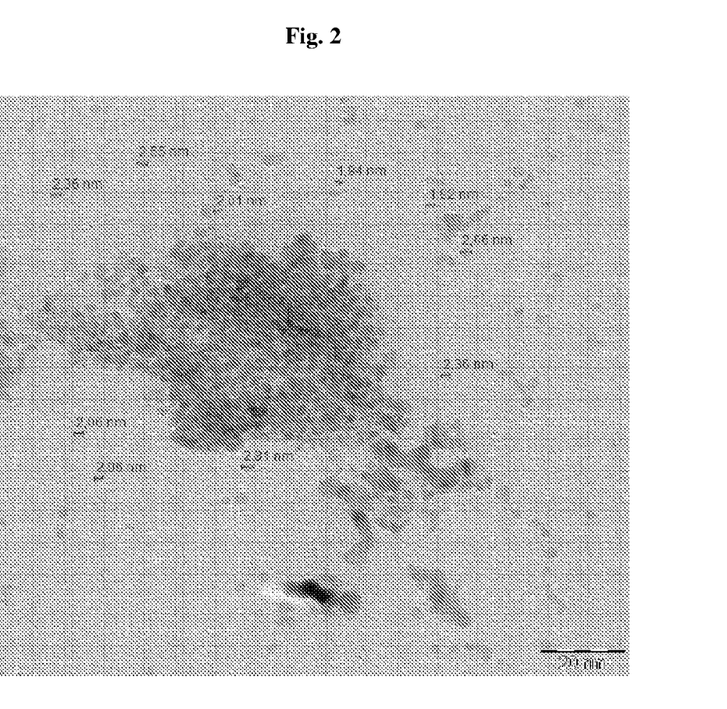
FIG. 2 presents a TEM micrograph of palladium nanoparticles obtained in Example 1A.

A TEM micrograph of palladium nanoparticles obtained by the described method is presented in FIG. 2.

Figure 3:
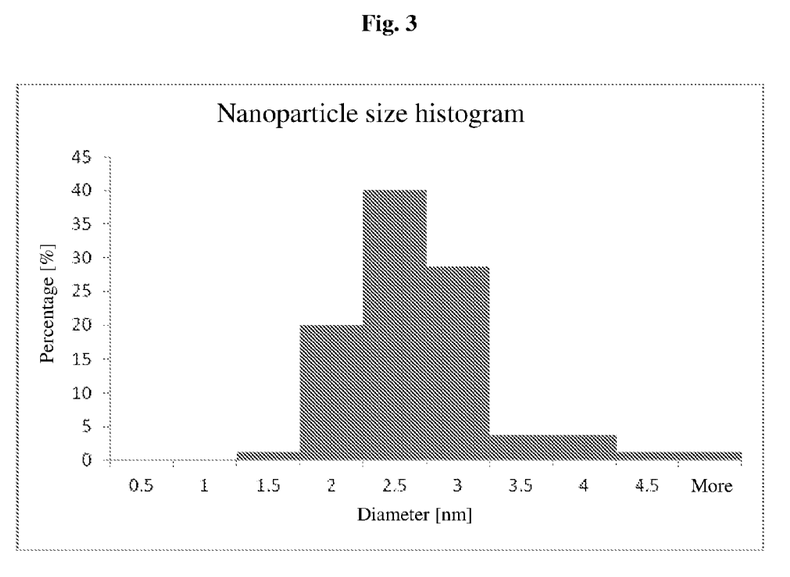
FIG. 3 presents a size distribution histogram of palladium nanoparticles obtained in Example 1A.

Diameter of the obtained palladium nanostructures ranges from 1.5 to 5 nm. A representative histogram of nanoparticle size distribution is presented in FIG. 3. By the method described in the present example nanoparticles having relatively narrow size distribution are obtained.

The purity for palladium nanoparticles was confirmed by electrochemical methods. A representative chronovoltamperometric curve for the obtained palladium nanoparticles is presented in FIG. 4. The curve was recorded for palladium nanoparticles, after they were transferred to a gold electrode, in 0.5 M solution of sulfuric acid. The polarization rate was 5 $mVs^{-1}$. The potential scale was presented in reference to the sulfate-mercury electrode.

Figure 4:
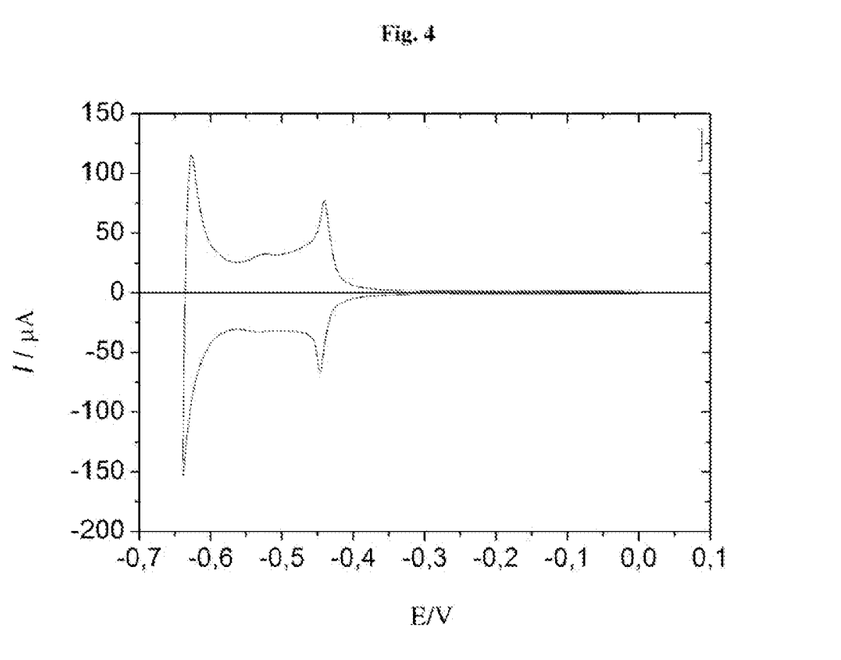
FIG. 4 presents a representative chronovoltamperometric curve for palladium nanoparticles obtained in Example 1A.

Peaks that are clearly apparent at potential $E=-0.43V$ indicate high purity of the material surface. Peaks related to the processes of hydrogen absorption and desorption from the nanoparticle depth are present at more cathodic potentials.

The presence of the hydrated oxides and/or palladium hydroxides at the surface of the newly formed palladium nanoparticles was also confirmed by the cyclic chronovoltamperometry (data not presented).

The colloid stability was investigated by comparing TEM micrographs of nanoparticles taken directly after reaction termination and 16 days after the nanoparticles were obtained (data not shown).

Figure 5A:
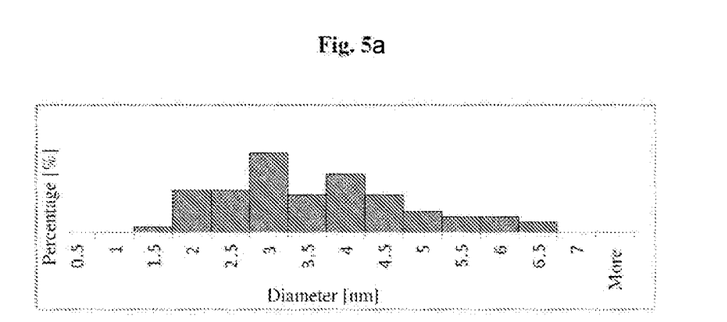
FIGS. 5a and 5b present representative size distribution histograms of palladium nanoparticles present in the supernatants after centrifuging a sample of the 16-day colloid obtained in Example 1A at 6 kRPM (FIGS. 5a) and 15 kRPM (FIG. 5b), respectively.
Figure 5B:
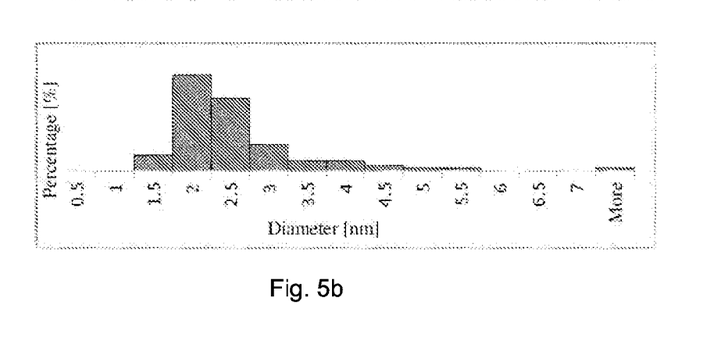

A possibility to fractionate the palladium nanoparticles based on their diameter was demonstrated by taking TEM micrographs of nanoparticles from the supernatant of the 16-day colloid after it was centrifuged at 6 kRPM and 15 kRPM, as presented in FIG. 5a and FIG. 5b, respectively.

B) Reduction reaction is carried out in the continuous flow system presented in FIG. 1a, in a Teflon tube having the inner diameter of 1/32" and length of 40 cm, wherein the flow rate of the reagents in the reaction tube is 200 ml/h.

Aqueous solution of 10 mM palladium (II) nitrate (Pd $(NO_3)_2$) in 10 mM $HNO_3$ (pH=2) is used to obtain a stable colloid of palladium nanoparticles. 20 mM aqueous solution of hydrazine is used as the reducing agent.

The reaction is carried out in temperature of 40° C., and 40 mM solution of hydrogen peroxide is used to terminate the reaction.

Figure 6:
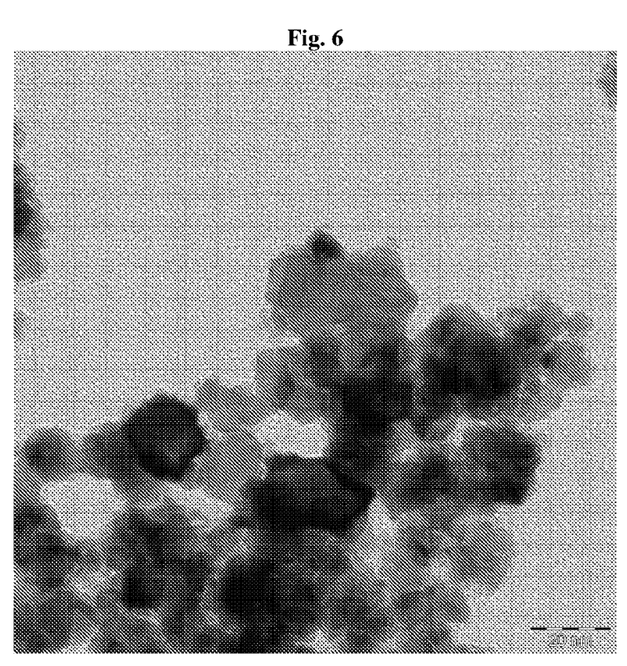
FIG. 6 presents a TEM micrograph of palladium nanoparticles obtained in Example 1B.

A black colloid of palladium nanoparticles is the product of the reaction. FIG. 6 presents a TEM micrograph of palladium nanoparticles obtained under such conditions. The diameter of the obtained palladium nanostructures amounts to about 15 nm C) Reduction reaction is carried out in the continuous flow system presented in FIG. 1a, in a Teflon tube having the inner diameter of 1/16" and length of 60 cm, wherein the flow rate of the reagents in the reaction tube is 320 ml/h.

Aqueous solution of 1 mM palladium (II) nitrate (Pd $(NO_3)_2$) is used to obtain a stable colloid of palladium nanoparticles. 2 mM aqueous solution of hydrazine is used as the reducing agent.

The reaction is carried out in temperature of 80° C., and 12.8 mM solution of hydrogen peroxide is used to terminate the reaction.

Figure 7:
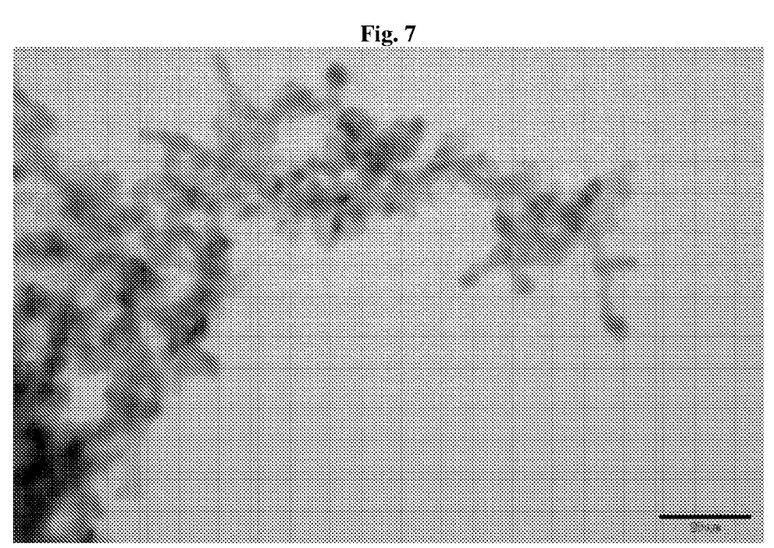
FIG. 7 presents a TEM migrograph of palladium nanoparticles obtained in Example 1C.

A stable black colloid of palladium nanoparticles is the product of the reaction. The colloid obtained is stable for a period of 2 months (or even longer) without a need for mixing and/or sonication in the ultrasonic bath. FIG. 7 presents a TEM micrograph of palladium nanoparticles obtained under such conditions. The diameter of the obtained palladium nanostructures amounts to about 3 nm.

The purity for palladium nanoparticles was confirmed by electrochemical methods. A representative chronovoltamperometric curve for the obtained palladium nanoparticles is presented in FIG. 8. The curve was recorded for palladium nanoparticles, after they were transferred to a gold electrode, in 0.5 M solution of sulfuric acid. The polarization rate was 5 $mVs^{-1}$. The potential scale was presented in reference to the sulfate-mercury electrode.

Figure 8:
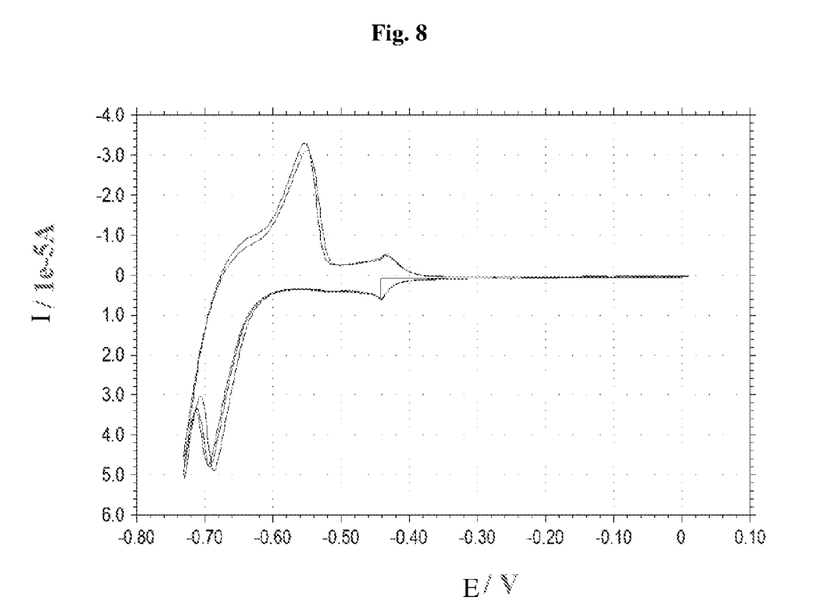
FIG. 8 presents a chronovoltamperometric curve for palladium nanoparticles obtained in Example 1C.

Peaks that are clearly apparent at potential $E=-0.43V$ indicate high purity of the material surface. Peaks related to the processes of hydrogen absorption and desorption from the nanoparticle depth are present at more cathodic potentials. The separation of these processes from the reaction of hydrogen evolution (below $E=-0.7$ V) is indicative of very small nanoparticle volume.

Reference Example

Synthesis of Palladium Nanoparticles without Addition of Hydrogen Peroxide

Nanostructure synthesis was carried out as described in Example 1A, except that no hydrogen peroxide solution is added.

An unstable black colloid of palladium nanoparticles is the product of the reaction. The metal concentration in the obtained colloid is high. Nevertheless the colloid is not stable and the nanoparticles undergo aggregation.

Example 2

Synthesis of Palladium Nanoparticles Having Controlled Size in a Powder Form A portion of the colloid obtained in Example 1A-C was centrifuged, subsequently dried and black powder was obtained.

Example 3

Synthesis of Copper (I) Oxide Nanoparticles of Controlled Size and Their Properties Characteristic Reduction reaction is carried out in the continuous flow system presented in FIG. 1a, in a Teflon tube having the inner diameter of 1/32" and length of 40 cm, wherein the flow rate of the reagents in the reaction tube is 200 ml/h.

Aqueous solution of 10 mM $Cu(NO_3)_2$ is used to obtain a stable colloid of copper (I) oxide nanoparticles. 20 mM aqueous solution of hydrazine is used as the reducing agent. The reaction is carried out in temperature of 40° C., and 3.79 mM solution of hydrogen peroxide with addition of 2.69 mM NaOH (pH≈12) is used to terminate the reaction. The obtained colloid solution has pH≈7.

A stable orange-yellow colloid of copper (I) oxide nanoparticles is the product of the reaction. The colloid obtained is stable for a period of 2 weeks (or even longer) without a need for mixing and/or sonication in the ultrasonic bath.

Figure 9:
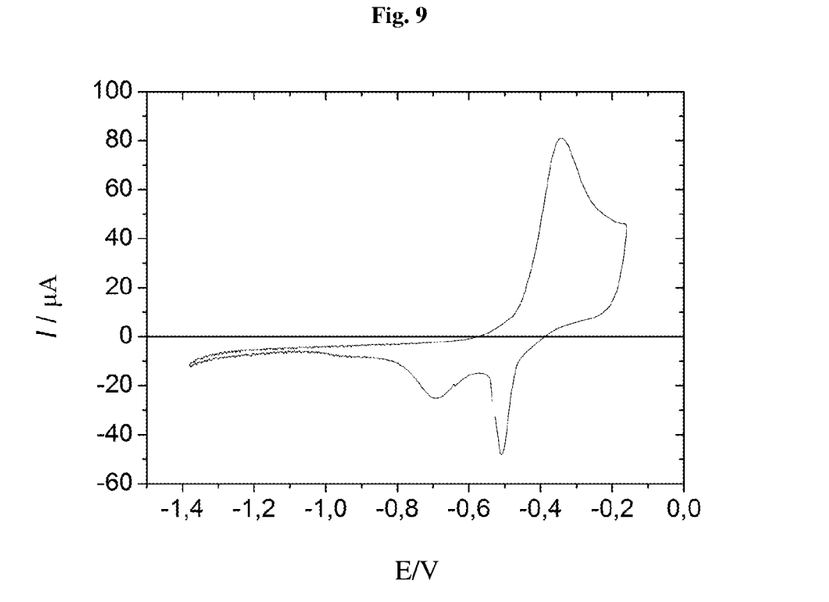
FIG. 9 presents a chronovoltamperometric curve for $Cu_2O$ nanoparticles obtained in Example 3.

A representative chronovoltamperometric curve for the obtained copper (I) oxide nanoparticles is presented in FIG. 9. The curve was recorded for copper (I) oxide nanoparticles, after they were transferred to a gold electrode, in a saturated solution of $Na_2CO_3$. The polarization rate was 5 $mVs^{-1}$. The potential scale was presented in reference to the sulfate-mercury electrode.

Figure 10:
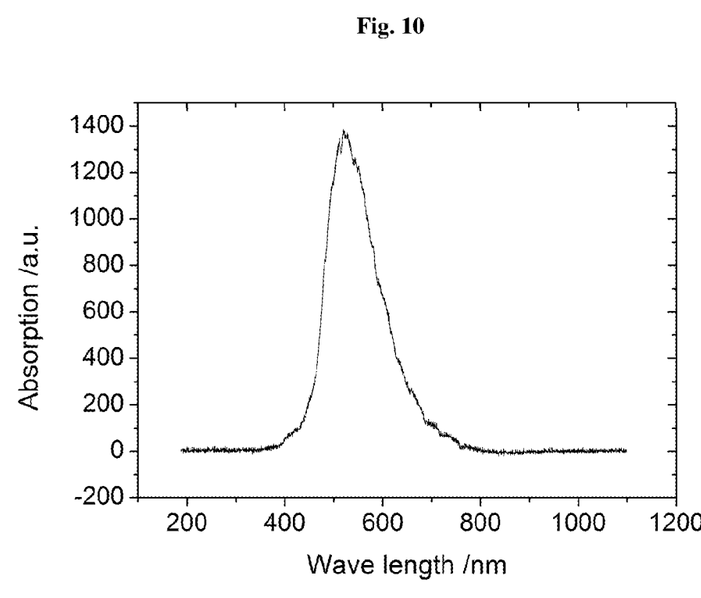
FIG. 10 presents a UV/VIS spectrum for $Cu_2O$ nanoparticles obtained in Example 3.

FIG. 10 presents a UV/VIS spectrum recorded for copper (I) oxide nanoparticles. The spectrum shows an absorption band ($\lambda_{max}$=525 nm) corresponding to surface plasmon resonance (SPR) characteristic for copper nanoparticles. The exact band position depends on the nanoparticle size (see Mott et al., "Synthesis of Size-Controlled and Shaped Copper Nanoparticles", Langmuir, 2007, 23, 5740-5745).

Figure 11:
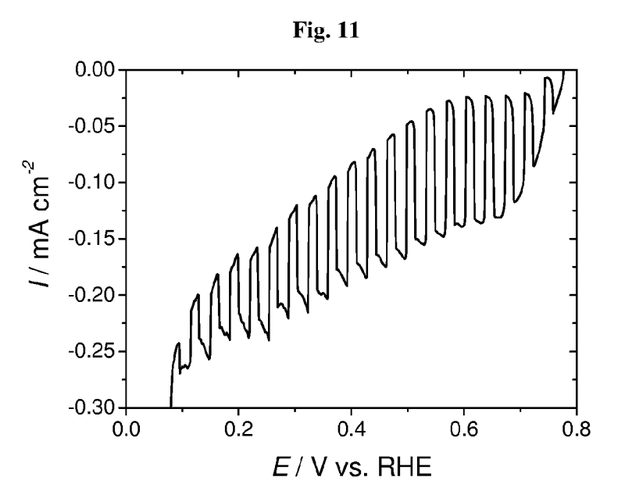
FIG. 11 presents a current-potential characteristics for $Cu_2O$ nanoparticles obtained in Example 3 under chopped illumination.

Nanoparticles of copper (I) oxide obtained by the described method also exhibit photocatalytic activity. FIG. 11 presents a chronovoltamperometric curve (a cathodic part) recorded for 50 μg of $Cu_2O$ nanoparticles obtained directly from synthesis on fluorine-doped tin oxide (FTO) electrode in a buffered solution (pH=9) of 1M $Na_2SO_4$. During polarization at the rate of 1 $mVs^{-1}$, the electrode was illuminated with a halogen lamp (100 $mWcm^{-2}$) equipped with a shutter comprising a mechanic diaphragm triggered every 3 seconds. Thus obtained curve displays a characteristic oscillation between light and dark currents.

This experiment confirms the photocatalytic activity of copper (I) oxide nanoparticles. The obtained nanoparticles 'direct from synthesis' (i.e. without further treatment or purification) exhibit substantial photocurrents with an order of magnitude amounting to about 50 μA $cm^{-2}$.

Resulting from the significant purity of nanoparticles obtained by the method of the invention, a possibility of their coating with a protective layer of other semiconductors using an ALD method in combination with the photocatalytic activity, renders this material useful as an active photocathode material in the process of water photoelectrolysis.

Figure 12:
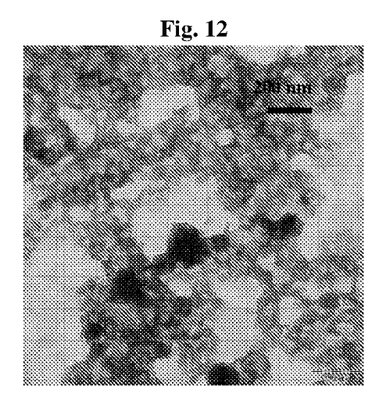
FIG. 12 presents a TEM micrograph of $Cu_2O$ nanoparticles obtained in Example 3.

FIG. 12 presents a TEM micrograph of $Cu_2O$ nanoparticles obtained under conditions described above.

Example 4

Synthesis of Gold Nanoparticles

Reduction reaction is carried out in the continuous flow system presented in FIG. 1a, in a Teflon tube having the inner diameter of 1/32" and length of 5 cm, wherein the flow rate of the reagents in the reaction tube is 100 ml/h.

Aqueous solution of 5 mM $HAuCl_4$ is used to obtain a stable colloid of gold nanoparticles. 3 mM aqueous solution of hydrazine is used as the reducing agent.

The reaction is carried out in temperature of 40° C., and 9.8 M solution of hydrogen peroxide is used to terminate the reaction.

A stable pink colloid of gold nanoparticles is the product of the reaction. The metal concentration in the obtained colloid amounts to about 350 ppm. The colloid obtained is stable for a period of 5 weeks (or even longer) without a need for mixing and/or sonication in the ultrasonic bath.

Figure 13:
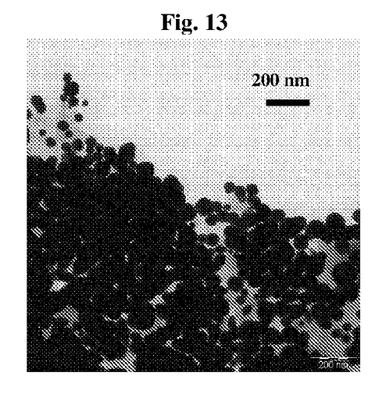
FIG. 13 presents a TEM micrograph of gold nanoparticles obtained in Example 4.

A TEM micrograph of gold nanoparticles obtained by the described method is presented in FIG. 13. Diameter of the obtained gold nanostructures is about 50 nm Example 5

Synthesis of Platinum Nanoparticles

Reduction reaction is carried out in the system presented in FIG. 1a, in a Teflon tube having the inner diameter of 1/32" and length of 40 cm, wherein the flow rate of the reagents in the reaction tube is 100 ml/h.

Aqueous solution of 10 mM $K_2PtCl_4$ is used to obtain a stable colloid of platinum nanoparticles. 20 mM aqueous solution of hydrazine is used as the reducing agent.

The reaction is carried out in temperature of 40° C., and 40 mM solution of hydrogen peroxide is used to terminate the reaction. A stable black colloid of platinum nanoparticles is the product of the reaction.

Example 6

Synthesis of Alloy Pd/Pt Nanoparticles

Reduction reaction is carried out in the system presented in FIG. 1a, in a Teflon tube having the inner diameter of 1/32" and length of 40 cm, wherein the flow rate of the reagents in the reaction tube is 200 ml/h.

Aqueous solution of 5 mM palladium (II) nitrate ($Pd(NO_3)_2$) and 5 mM platinum (II) nitrate ($Pt(NO_3)_2$) is used to obtain a stable colloid of palladium—platinum alloy nanoparticles. 20 mM aqueous solution of hydrazine is used as the reducing agent.

The reaction is carried out in temperature of 40° C., and 35 mM solution of hydrogen peroxide is used to terminate the reaction.

A stable black colloid of Pd/Pt alloy nanoparticles is the product of the reaction. The colloid obtained is stable for a period of 2 weeks (or even longer) without a need for mixing and/or sonication in the ultrasonic bath.

Example 7

Synthesis of Core-Shell Type Nanoparticles of Copper and Palladium

Reduction reaction is carried out in the continuous flow system presented in FIG. 1b, in a Teflon tube having the inner diameter of 1/32" and length of 40 cm for each of the two steps, wherein the flow rate of the reagents in the reaction tube is 200 ml/h in the first step and 300 ml/h in the second step.

In the first step a solution of 10 mM $Cu(NO_3)_2$ undergoes a reduction reaction using 20 mM aqueous solution of hydrazine as the reducing agent. In the second step a solution of 10 mM $Pd(NO_3)_2$ is fed to the reaction mixture. 3.79 mM solution of hydrogen peroxide with addition of 2.69 mM NaOH is used to terminate the reaction.

A stable colloid of nanoparticles is the product of the reaction. It is stable for a period of 2 weeks (or even longer) without a need for mixing and/or sonication in the ultrasonic bath.

Example 8

X-ray powder diffraction analysis of $Cu_2O$, Au, Pt and Pd nanoparticles

The presence of metal oxides, such as Pd0 or $Cu_2O$, to the extend dependent on concentration of hydrogen peroxide and pH of the solution, was confirmed by X-ray powder diffraction.

The X-ray diffractograms were registered in Bragg-Brentano geometry with the X-Pert Philips diffractometer, using a tube with a copper anode, supplied with a current of 30 mA at voltage of 40 kV, and a curved graphite monochromator. The wavelength of radiation ($\lambda CuK\alpha$) amounted to 1.54178 Å. The diffraction lines were recorded by "step-scanning" method in the range from 20° to 140° 2θ and 0.05° step.

Figure 14:
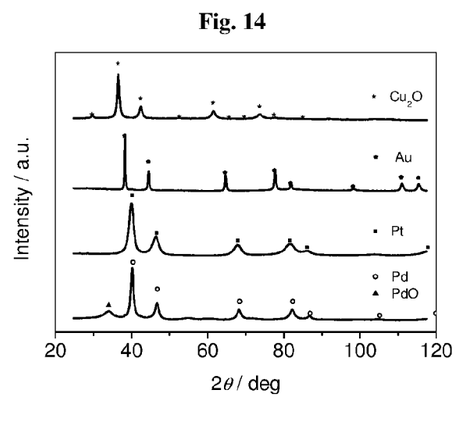
FIG. 14 presents X-ray diffraction patterns registered for $Cu_2O$, Au, Pt and Pd nanoparticles according to Example 8.

FIG. 14 presents X-ray diffractograms for 10 nm palladium nanoparticles, 50 nm gold nanoparticles, 5 nm platinum nanoparticles and 10 nm copper (I) oxide nanoparticles.

Diffractograms indicate the presence of metal oxides and lack of other crystalline phases, apart from the metals and oxides thereof. Moreover, broadening of half-width at maximum intensity (FWHM) is an evidence of nanocrystalline phase presence.

Example 9

Use of Palladium Nanoparticle Colloid as a Catalyst

In the present Example palladium nanoparticles synthesized in Example 1A were used as a catalyst in the Suzuki reaction.

The Suzuki reaction plays an important role in organic synthesis of polyalkenes, styrene derivatives and substituted diaryl compounds. Because of availability and low prices of phenylboronic acids, the Suzuki reaction is a method widely used by pharmaceutical industry [Przemyst Chemiczny 3/2012].

Palladium nanoparticles obtained by the method of the invention exhibit significantly higher catalytic activity in the Suzuki reaction than palladium nanoparticles stabilized by PVP. This is due to blocking of the catalyst active sites by PVP. A decrease in Pd catalyst activity together with the surfactant concentration increase was described by Narayanan et al. [Radha Narayanan and Mostafa A. El-Sayed, *J. Am. Chem. Soc.*, 2003, 125 (27), p. 8340-8347].

In the following reaction after 1 hour of synthesis in 40° C. and in the presence of Pd nanoparticles as a catalyst, significantly larger amounts of biphenyl were obtained in case of pure nanoparticles in comparison to the synthesis in which PVP stabilized nanoparticles are used.

This example shows that nanoparticles of the invention can be used directly as heterogenic catalysts.

Example 10

Modification of Palladium and Copper Nanoparticles with Paracetamol

Palladium nanoparticles obtained in Example 1A and copper nanoparticles obtained in Example 3 were incubated in paracetamol solution for 1 day, without their prior purification.

After rinsing the nanoparticles were analyzed by spectroscopic means and the presence of paracetamol adsorbed at the nanoparticle surface was demonstrated.

This example shows that nanoparticles obtained by the method of the invention can be modified directly after synthesis with therapeutic substances and used in treatment.

The invention claimed is:

1. A method of synthesis of nanoparticles of controlled size in a continuous-flow system, and wherein the said continous-flow system comprises tubing, in which a stream of reagents and products flows in a continuous manner, and wherein the said method comprises at least one step in which a precursor substance solution undergoes a reduction reaction using a reducing agent solution and nanoparticles are produced, characterized in that the reduction reaction is terminated by adding a substance neutralizing the reducing agent, wherein the reduction reaction is carried out in the absence of stabilizing agents other than said substance neutralizing the reducing agent, and wherein a nanoparticle colloid is produced.

2. The method of claim 1, wherein the method comprises one step, in which the precursor substance solution undergoes the reduction reaction using the reducing agent solution and homogeneous nanoparticles are obtained.

3. The method of claim 1, wherein the method comprises at least two steps, in which the precursor substance solution undergoes the reduction reaction using the reducing agent solution and layered nanoparticles of core-shell type are obtained.

4. The method of claim 1, wherein the precursor substance is a metal precursor or a mixture of metal precursors.

5. The method of claim 4, wherein the metal precursor is a metal salt or a mixture of different metal salts.

6. The method of claim 5, wherein the metal salt is a salt of a metal selected from a group consisting of palladium, silver, gold, platinum, ruthenium, osmium, iridium, rhodium, nickel, cobalt, copper and iron.

7. The method of claim 1, wherein the precursor substance is a salt selected from the group comprising of $AgNO_3$, $AgClO_4$, $AgHSO_4$, $Ag_2SO_4$, $AgF$, $AgBF_4$, $AgPF_6$, $CH_3COOAg$, $AgCF_3SO_3$, $CuCl_2$, $Cu(NO_3)_2$, $CuSO_4$, $Cu(HSO_4)_2$, $Cu(ClO_4)_2$, $CuF_2$, $(CHCOO)_2Cu$, $H_2PtCl_6$, $H_6Cl_2N_2Pt$, $PtCl_2$, $PtBr_2$, $K_2[PtCl_4]$, $Na_2[PtCl_4]$, $Li_2[PtCl_4]$, $H_2Pt(OH)_6Pt(NO_3)_2$, $[Pt(NH_3)_4]Cl_2$, $[Pt(NH_3)_4](HCO_3)_2$, $[Pt(NH_3)_4](OAc)_2$, $(NH_4)_2PtBr_6$, $K_2PtCl_6$, $PtSO_4$, $Pt(HSO_4)_2$, $Pt(ClO_4)_2$, $H_2PdCl_6$, $H_6Cl_2N_2Pd$, $PdCl_2$, $PdBr_2$, $K_2[PdCl_4]$, $Na_2[PdCl_4]$, $Li_2[PdCl_4]$, $H_2Pd(OH)_6$, $Pd(NO_3)_2$, $[Pd(NH_3)_4]Cl_2$, $[Pd(NH_3)_4](HCO_3)_2$, $[Pd(NH_3)_4](OAc_2)$, $(NH_4)_2PdBr_6$, $(NH_3)_2PdCl_6$, $PdSO_4$, $Pd(HSO_4)_2$, $Pd(ClO_4)_2$, $HAuCl_4$, $AuCl_3$, $AuCl$, $AuF_3$, $(CH_3)_2SAuCl$, $AuF$, $AuCl(SC_4H_8)$, $AuBr$, $AuBr_3$, $Na_3Au(S_2O_3)_2$, $HAuBr_4$, $K[Au(CN)_2]$, $CoF_2$, $Co(NO_3)_2$, $CoCl_2$, $CoSO_4$, $Co(HSO_4)_2$, $Co(ClO_4)_2$, $(CHCOO)_2Co$, $CoBr_2$, $[Co(NH_3)_6]Cl_3$, $[CoCl(NH_3)_5]Cl_2$, $[Co(NO_2)(NH_3)_5]Cl_2$, $NiF_2$, $Ni(NO_3)_2$, $NiCl_2$, $NiSO_4$, $Ni(HSO_4)_2$, $Ni(ClO_4)_2$, $(CHCOO)_2Ni$, $NiBr_2$, $Ni(OH)SO_4$, $Ni(OH)Cl$, $FeF_2$, $Fe(NO_3)_2$, $FeCl_2$, $FeSO_4$, $Fe(HSO_4)_2$, $Fe(ClO_4)_2$, $(CHCOO)_2Fe$, $FeBr_2$, $FeF_3$, $Fe(NO_3)_3$, $FeCl_3$, $Fe_2(SO_4)_3$, $Fe(HSO_4)_3$, $Fe(ClO_4)_3$, $(CHCOO)_3Fe$, $FeBr_3$, $RuCl_2$, $((CH3)_2SO)_4$, $RuCl_3$, $[Ru(NH_3)_5(N_2)]Cl_2$, $Ru(NO_3)_3$, $RuBr_3$, $RuF_3$, $Ru(ClO_4)_3$, $OsI$, $OsI_2$, $OsBr_3$, $OsCl_4$, $OsF_5$, $OsF_6$, $OsOF_5$, $OsF_7$, $IrF_6$, $IrCl_3$, $IrF_4$, $IrF_5$, $Ir(ClO_4)_3$, $K_3[IrCl_6]$, $K_2[IrCl_6]$, $Na_3[IrCl_6]$, $Na_2[IrCl_6]$, $Li_3[IrCl_6]$, $Li_2[IrCl_6]$, $[Ir(NH_3)_4Cl_2]Cl$, $RhF_3$, $RhF_4$, $RhCl_3$, $[Rh(NH_3)_5Cl]Cl_2$, $RhCl[P(C_6H_5)_3]_3$, $K[Rh(CO)_2Cl_2]$, $Na[Rh(CO)_2Cl_2]$, $Li[Rh(CO)_2Cl_2]$, $Rh_2(SO_4)_3$, $Rh(HSO_4)_3$ and $Rh(ClO_4)_3$, their hydrates or mixtures of these salts and/or hydrates.

8. The method of claim 1, wherein the reducing agent is selected from a group comprising hydrazine, ascorbic acid, sodium borohydride, sodium hypophosphite, lithium tetraethylborohydride, methanol, 1,2-hexadecanediol, hydroxylamine and dimethylborazane (DMAB).

9. The method of claim 1, wherein the substance neutralizing the reducing agent is selected from a group comprising hydrogen peroxide, oxygen, ozone, $NO_2$ and a redox buffer.

10. The method of claim 1, wherein the tubing comprises a plurality of tubing segments and at least two tubing segments are maintained at different temperatures.

11. The method of claim 1, wherein the precursor substance is $Pd(NO_3)_2$, the reducing agent is hydrazine, and the substance neutralizing the reducing agent is hydrogen peroxide.

12. The method of claim 1, wherein precursor substance is $Cu(NO_3)_2$, the reducing agent is hydrazine, and the substance neutralizing the reducing agent is hydrogen peroxide, wherein the solution of the substance neutralizing the reducing agent is provided in the form of a solution that further comprises NaOH.

13. The method of claim 12, wherein in the first step the solution of the precursor substance $Cu(NO_3)_2$ undergoes the reduction reaction using hydrazine solution, which results in formation of the copper core, and in the second step to the reaction mixture the solution of the precursor substance $Pd(NO_3)_2$ is supplied, whose reduction results in formation of the palladium shells on the copper nanoparticles formed in the first step, and the reduction reaction is terminated by addition of hydrogen peroxide solution and a base, wherein the base concentration is sufficient to ensure neutral pH of the product stream.

14. The method of claim 1, wherein the precursor substance is a mixture of $Pd(NO_3)_2$ and $Pt(NO_3)_2$, whose reduction results in formation of homogenous nanoparticles of Pd/Pt alloy.

15. The method of claim 1, wherein the nanoparticles comprises a metal core and a metal outer layer, and the substance neutralizing the reducing agent is a redox buffer having a potential resulting in an under-potential reduction of the metal outer layer on the metal core.

16. The method of claim 1, wherein the method comprises further a step of colloid nanoparticle centrifugation and/or drying, wherein nanoparticle powder is obtained.

17. The method of claim 1 wherein the substance neutralizing the reducing agent is a redox buffer.

18. The method of claim 17 wherein the redox buffer comprises a redox pair having an oxidized (ox) and a reduced (red) form whose concentrations [ox] and [red] respectively are such that log([ox]/[red]) is in the range of −2 to +2.

19. The method of claim 17, wherein the redox buffer is selected from the group consisting of the following redox pairs: $Fe(CN)_6^{3-}/Fe(CN)_6^{4-}$, $Fe^{3+}/Fe^{2+}$, $[Co(bipy)_3]^{2+}/[Co(bipy)_3]^{3+}$, $Co(phen)_3^{3+}/Co(phen)_3^{2+}$, $[Ru(bipy)_3]^{3+}/[Ru(bipy)_3]^{2+}$, $[Ru(NH_3)_6]^{3+}/[Ru(NH_3)_6]^{2+}$ $[Ru(CN)_6]^{3-}/[Ru(CN)_6]^{4-}$, $Fe(phen)_3^{3+}/Fe(phen)_3^{2+}$, $Ce^{4+}/Ce^{3+}$, NADH/NAD+.

20. The method of claim 1 wherein the reducing agent is hydrazine and the substance neutralizing the reducing agent is hydrogen peroxide.

21. The method of claim 1 wherein the surface of said nanoparticles is substantially free of surfactants and other organic molecules.

22. The method of claim 1 wherein nanoparticles having diameters in the range from 1 to 50 nm are obtained.

23. The method of claim 22, wherein nanoparticles having diameters in the range from 3 to 10 nm are obtained.

* * * * *